United States Patent
Okada

(10) Patent No.: US 9,511,080 B2
(45) Date of Patent: Dec. 6, 2016

(54) OKADAELLA GASTROCOCCUS AND CANCER

(75) Inventor: Takayuki Okada, Brisbane (AU)

(73) Assignee: Okada Medical Services Pty Ltd, Queensland (AU)

(*) Notice: Subject to any disclaimer, the term of this patent is extended or adjusted under 35 U.S.C. 154(b) by 20 days.

(21) Appl. No.: 13/519,555

(22) PCT Filed: Dec. 23, 2010

(86) PCT No.: PCT/AU2010/001739
§ 371 (c)(1),
(2), (4) Date: Feb. 8, 2013

(87) PCT Pub. No.: WO2011/079349
PCT Pub. Date: Jul. 7, 2011

(65) Prior Publication Data
US 2013/0172298 A1   Jul. 4, 2013

Related U.S. Application Data

(60) Provisional application No. 61/291,452, filed on Dec. 31, 2009.

(51) Int. Cl.
| | |
|---|---|
| *A61K 31/4439* | (2006.01) |
| *A61K 31/496* | (2006.01) |
| *A61K 31/65* | (2006.01) |
| *A61K 31/00* | (2006.01) |
| *A61K 31/4184* | (2006.01) |
| *A61K 45/06* | (2006.01) |
| *G01N 33/574* | (2006.01) |
| *A61K 31/43* | (2006.01) |
| *A61K 31/4709* | (2006.01) |
| *A61K 31/5383* | (2006.01) |

(52) U.S. Cl.
CPC ............ *A61K 31/65* (2013.01); *A61K 31/00* (2013.01); *A61K 31/4184* (2013.01); *A61K 31/43* (2013.01); *A61K 31/4439* (2013.01); *A61K 31/4709* (2013.01); *A61K 31/496* (2013.01); *A61K 31/5383* (2013.01); *A61K 45/06* (2013.01); *G01N 33/57407* (2013.01); *G01N 2333/315* (2013.01)

(58) Field of Classification Search
None
See application file for complete search history.

(56) References Cited

U.S. PATENT DOCUMENTS

| | | | |
|---|---|---|---|
| 6,221,864 B1 | 4/2001 | Hirayama et al. | |
| 6,261,824 B1* | 7/2001 | Okada | 435/243 |
| 6,489,317 B1* | 12/2002 | Borody | 514/197 |
| 2004/0180850 A1 | 9/2004 | Natunen et al. | |
| 2005/0014797 A1* | 1/2005 | Ieni | 514/338 |

FOREIGN PATENT DOCUMENTS

| | | |
|---|---|---|
| WO | 2004089340 | 10/2004 |
| WO | WO 2004089340 A1 * | 10/2004 |

OTHER PUBLICATIONS

Okada et al., Cases of gastric MALT lymphoma and diffuse large B-cell lymphoma associated with *Okadaella gastrococcus*-like organism, Gastroenterology, (Apr. 2007) vol. 132, No. 4, Suppl. 2, p. A311, STN document No. PREV200700603939, entered STN: Dec. 6, 2007.*

Okada et al., The Development of Gastric Cancer Associated with *Okadaella gastrococcus* (Og) Infection Following *Helicobacter pylori* (Hp) Eradication: A Case Report, American Journal of Gastroenterology, (Sep. 2005) vol. 100, No. 9, Suppl. S, pp. S61, available at http://www.nature.com/ajg/journal/v100/n9s/full/ajg2005522a.html.*

Cianci et al., Third-line rescue therapy for *Helicobacter pylori* infection, World J Gastroenterol. Apr. 21, 2006;12(15):2313-9.*

Kuwayama et al., Rabeprazole-based eradication therapy for *Helicobacter pylori*: a large-scale study in Japan, Alimentary Pharmacology and Therapeutics, (May 2007) vol. 25, No. 9, pp. 1105-1113, STN accession No. 2007182826.*

Strehl, Furazolidone, tetracycline and omeprazole: a low-cost alternative for *Helicobacter pylori* eradication in children, Jornal de pediatria, (Mar.-Apr. 2008) vol. 84, No. 2, pp. 160-5, STN accession No. 2008215977.*

Alkan et al., Regression of salivary gland MALT lymphoma after treatment for *Helicobacter pylori*, Lancet (England), (Jul. 27, 1996) vol. 348, pp. 268-269, STN document No. 33-14654.*

Cianci et al. (2006) "Third-Line Rescue Therapy for *Helicobacter pylori* Infection" World J Gastroenterol 12 (15):2313-2319.

Okada et al. (2003) "Pathogenic Virulence of *Okadaella gastrococcus* (PVOg): Ultrastructural Studies In vivo and In vitro" Gastroenterol vol. 124, No. 4, Supplement 1, p. A-270, Abstract M898.

* cited by examiner

*Primary Examiner* — Svetlana M Ivanova

(74) *Attorney, Agent, or Firm* — Michael B. Rubin; Bozicevic, Field & Francis LLP

(57) ABSTRACT

The present invention provides compositions, methods of manufacture, process and uses for diagnosing, preventing, inhibiting, and treating the development and proliferation of diseases and disorders associated with *Okadaella gastrococcus* (Og) bacterial infection in a patient.

13 Claims, 8 Drawing Sheets

THE COREA PATHWAY

OKADAELLA GASTROCOCCUS AND CANCER

CROSS-REFERENCE TO RELATED APPLICATIONS

This present application is a United States national phase application of International application No. PCT/AU2010/001739 filed Dec. 23, 2010 which claims the benefit of priority from United States Provisional Patent Application Ser. No. 61/291,452 filed Dec. 31, 2009, the entire content of which is hereby incorporated by reference.

FIELD OF THE INVENTION

This invention is in the field of predicting, preventing and treating diseases and disorders associated with *Okadaella gastrococcus* (Og) bacterial infection. In particular, this invention relates to the etiological involvement of the Og bacterium in conditions other than gastrointestinal erosion and ulcers, to include cancer of various organs and tissues.

BACKGROUND OF THE INVENTION

It has previously been shown (by this inventor) that the bacterium *Okadaella gastrococcus* (Og) directly contributes to the etiology of gastro-duodenitis and ulcerations in a manner similar to *Helicobacter pylori* (Hp). U.S. Pat. No. 6,261,824, entitled "Gram Negative Coccoid Bacterium *Okadaella Gastrococcus*", which is hereby incorporated by reference in its entirety, discloses the characteristics of this newly isolated bacterium, and methods of detecting its presence in an infected patient. The inventor has now made the discovery that Og is directly contributory to a variety of diseases and disorders in a patient, such as the etiology of cancer in various tissues and organs. Og can also co-exist with Hp in a patient's bodily tissue and fluids-[Og(+)/Hp(+)], or it can exist alone-[Og(+)/Hp(−)].

There are approximately 1.2 million new cases of cancer in the world per year. An overwhelming body of evidence indicates that certain types of pathogens (viruses and bacteria) play a direct role in the etiology of cancers, and that up to 15% of malignancies worldwide are attributable to infections. Although the mechanism involved in most cases remains unclear, one dominant theory is that genetic factors may predispose patients to "cancer causing" bacterial infections, and that infections cause chronic inflammation, as well as immune invasion and suppression. Bacterial infections linked to cancer include: *Salmonella typhi* to gallbladder cancer; *Streptococcus bovis* to colon cancer; *Chlamydophila pneumoniae* to lung cancer; and *Helicobacter pylori* (Hp) to gastric cancer and mucosa-associated lymphoid tissue (MALT) lymphoma (Mager, D. L., 2006).

Gastric cancer is the fourth most common cancer worldwide, and the second leading cause of cancer related deaths. Hp is now recognized as the primary cause of gastric cancer wherein gastric infection of Hp leads to a 2.1-6.7 increased cancer risk. It has therefore been designated a class 1 carcinogen. In Western countries, e.g. USA and Europe, the incidence of Hp infection is declining, and is presently believed to infect about 30% of the population. The concurrent incidence of distal gastric cancer in this population is about 0.1-1.0%. In Asian countries, such as China and Japan, the Hp infection rate is 60-80% of the population, with a particularly high mortality rate from gastric cancer in Japan that is believed to be due to an extremely virulent Hp strain (Prinz et al, 2006).

Hp and Og infections are not limited to the gastrointestinal system. There is now emerging scientific evidence that both may be involved in the etiology of cancer in non-gastric tissues and organs. In a study involving 43 patients with non-small cell lung cancer, the Hp IgG antibody count was significantly higher in cancer patients than in control groups (Ece et al, 2005). And other research groups have reported that infection with certain Hp strains may lead to a 21-fold increase in relative risk for the development of lung cancer (Prinz et al, 2006). There have also been assertions that *Helicobacter* subspecies (spp.) microorganisms of various strains have been detected in bodily tissues and fluids located throughout the body (See US patent application 20060078919, entitled "Diagnostic Test Kit and Methods of Diagnosis and Treatment of *Helicobacter* Spp Associated Infections"). For example, 20060078919 discloses that *Helicobacter* spp. has been detected in a feline oral lesional mass of cancer cells; in a case of human tongue invasive squamous cell carcinoma; surrounding an osteocarcinoma in a canine leg; in malignant melanoma of a feline eyelid; and in the left ventricle heart muscle cells in a human with myocardial degeneration.

There is therefore a need within the medical community for determining the contributory factor of the bacterial strain Og in the etiology of a disease state, such as cancer. This assessment would also include determining the relative risk of a patient developing gastric and non-gastric cancer as a result of this infection.

There is also a need for efficacious therapeutic treatments to significantly reduce or eradicate Og detected in various fluids, tissues, and organs of a patient who is Og(+)/Hp(+) or Og(+)/Hp(−). This is based on evidence from previous studies that have shown that blocking pathogen proliferation in a disease state, such as cancer, contributed to a successful therapeutic outcome, especially if administered prior to a "point-of-no-return" or a pre-cancerous state.

SUMMARY OF THE INVENTION

This invention is based on the detection by the inventor of *Okadaella gastrococcus* (Og) in tissues and organs of human patients suffering from gastric and non-gastric cancers and precancerous conditions at levels that exceed the prevalence of *Helicobacter pylori* (Hp), indicating a role for Og in the development of gastric and/or non-gastric diseases and disorders.

Accordingly, the present invention is related to an association of Og with gastric and/or non-gastric diseases and disorders, especially gastric and/or non-gastric cancer e.g., carcinoma and/or and lymphoma. For example, the inventor demonstrates herein an association of Og with gastric adenocarcinoma and/or non-gastric adenocarcinoma and/or mucosa-associated lymphoid tissue (MALT) lymphoma and/or B cell lymphoma.

The present invention is also related to an association of Og with a risk of developing a cancer, especially a gastric cancer such as e.g., gastric adenocarcinoma. For example, the inventor demonstrates herein an association of Og with different stages of the so-called Correa Pathway leading to development of gastric carcinoma e.g., in superficial gastritis and/or chronically-inflamed gastric mucosa and/or atrophic gastritis and/or intestinal metaplasia and/or spasmolytic polypeptide-expressing metaplasia (SPEM) and/or dysplasia. In one example, the present invention relates particularly to the association of Og with gastric mucosa at a stage of the Correa Pathway preceding or including intestinal metaplasia e.g., in superficial gastritis and/or chronically-inflamed gastric mucosa and/or atrophic gastritis, and preferably in gastric mucosa exhibiting atrophic gastritis and/or intestinal metaplasia, because such a stage may represent a point at which a prognosis of a risk of developing a gastric cancer is most accurate, and/or at which prophylaxis remains effective. For the purposes of nomenclature, it is to be understood from the disclosure herein e.g., Table 2 hereof, that: (i) a Stage 1 condition may comprise normal mucosa and/or superficial gastritis and/or chronically-inflamed gastric mucosa in the Correa Pathway leading to adenocarcinoma, or alternatively, a Stage $I_E$, $I_{E1}$ or $I_{E2}$ lymphoma; (ii) a Stage 2 condition may comprise atrophic gastritis and/or intestinal metaplasia of type I or II or III and/or dysplasia in the Correa Pathway leading to adenocarcinoma, or alternatively, a Stage $I_E$, $I_{E1}$ or $I_{E2}$ lymphoma; and (iii) a Stage 3 condition will generally comprise a gastric adenocarcinoma, or alternatively, a Stage $II_E$, $II_{E1}$, $II_{E2}$, $III_E$ or $IV_E$ lymphoma.

This invention provides methods of preventing or treating the onset and/or the proliferation of diseases and disorders associated with Og infection, including gastric and non-gastric conditions, such as by reducing a level of Og in a patient or eradication of Og and, when Hp is also present, reducing a level of Hp or eradicating Hp. Treatment preferably occurs before the onset of severe histological changes, such as atrophy and intestinal metaplasia in adenocarcinomas, and before the onset of Stage $II_E$ in lymphomas. Preferably, the patients are human.

For example, the invention provides a method for treating or preventing the cause of a *Okadaella gastrococcus* (Og)-associated disorder or disease, comprising detecting the presence of Og-associated with said diagnosed disease or disorder in at least one bodily tissue or a body fluid of a patient, assessing the stage of said disease or disorder; and administering a treatment to said patient appropriate for said stage. Exemplary body tissues in which Og is detected include e.g., gastric mucosa, intestinal mucosa, gastric ulcer or a vessel or lamina propria thereof, stomach tissue, esophagus, gastroesophageal junction, lymphoid tissue, lymph node, colon, lung, occula adnexa, thyroid, salivary gland, brain, heart, bone, bone marrow, pancreas, liver, gall bladder, breast, overy, uterus, muscle, or neural-tissue, or a biopsy of such tissues, Exemplary body fluids in which Og is detected include e.g., blood or fraction thereof comprising erythrocytes, and fluids in connection with any of the foregoing tissues and biopsy samples.

In another example, the present invention provides a method of treatment or prevention of an Og-associated disease or disorder comprising administering a composition comprising a proton pump inhibitor to a subject in need thereof, preferably in combination with at least one antibiotic. The proton pump inhibitor and at least one antibiotic may be administered in combination e.g., sequentially or simultaneously.

Exemplary antibiotic therapy comprises administering to a patient at least one of amoxicillin, tetracycline e.g., doxycycline, one or more quinolones, azithromycin, or rifampicin, or a combination thereof. A plurality of antibiotics may be administered in combination e.g., sequentially or simultaneously. Preferably, the treatment or prevention reduces a level of *Okadaella gastrococcus* in the subject, e.g.; in the gastric mucosa or other bodily tissue or in a body fluid of the subject. More preferably, the treatment or prevention eradicates *O. gastrococcus* from the subject. The treatment may comprise a therapeutically effective amount of antibiotic therapy with proton pump inhibitor therapy, or proton pump inhibitor therapy alone.

Such therapy is preferably administered to a subject suffering from a Stage 1 condition such as an adenocarcinoma or lymphoma e.g., in a subject having chronically-inflamed gastric mucosa or Stage $I_E$, $I_{E1}$ or $I_{E2}$ lymphoma, for a suitable period to achieve a reduction in Og level. For example, the therapy may comprise administering a combination comprising amoxicillin, tetracycline, and one or more proton pump inhibitors to the subject for 1 or 2 or 3 weeks; and then administering a combination comprising amoxicillin, one or more quinolones, and one or more proton pump inhibitors to the subject for 3 or 4 or 5 weeks; and then administering one or more proton pump inhibitors to the subject for 4 or 5 or 6 or 7 or 8 or 9 or 10 weeks. In another example, a Stage 1 condition is treated by administering one or more tetracyclines e.g., doxycycline, and one or more quinolones, and one or more proton pump inhibitors to a subject in need thereof for 1 or 2 or 3 or 4 or 5 or 6 weeks, and then administering one or more proton pump inhibitors to the subject for 6 or 7 or 8 or 9 or 10 weeks. Exemplary patients suffering from a Stage 1 condition will be infected with Og but not with Hp, however they may be actively-infected with both Og and Hp.

Alternatively, therapy is preferably administered to a subject suffering from a Stage 2 condition, such as a Stage 2 adenocarcinoma or Stage 2 lymphoma, for a suitable period to achieve a reduction in Og level. For example, the therapy may comprise administering a combination comprising amoxicillin, tetracycline, and one or more proton pump inhibitors to a subject in need thereof for 1 or 2 or 3 or 4 weeks, and then administering a combination comprising amoxicillin, one or more quinolones, and one or more proton pump inhibitors to the subject for 3 or 4 or 5 or 6 weeks, and then administering to the subject one or more proton pump inhibitors for 5 or 6 or 7 or 8 or 9 or 10 weeks. In another example, a Stage 2 condition is treated by administering to a subject in need thereof a tetracycline e.g., doxycycline and one or more quinolones and one or more proton pump inhibitors for up to about 8 weeks e.g., for 3 or 4 or 5 or 6 or 7 or 8 weeks, and then administering to the subject one or more proton pump inhibitors for a further 6 or 7 or 8 or 9 or 10 weeks. Exemplary patients suffering from a Stage 2 condition will be infected with Og but not with Hp, however they may be actively-infected with both Og and Hp.

Alternatively, therapy is preferably administered to a subject suffering from a Stage 3 condition; such as a Stage 3 adenocarcinoma or Stage 3 lymphoma, for a suitable period to achieve a reduction in Og level. For example, the therapy may comprise administering a combination comprising amoxicillin, tetracycline, and one or more proton pump inhibitors for 1 or 2 or 3 or 4 weeks, and then administering a combination comprising amoxicillin, one or more quinolones, and one or more proton pump inhibitors for 3 or 4 or 5 or 6 weeks; and then administering a combination comprising tetracycline e.g., doxycycline, one or more quinolones, and proton pump inhibitors. In another example, a patient suffering a Stage 3 condition is administered a therapeutically-effective amount of one or more quinolones, tetracyclines, and proton pump inhibitors for up to about 6 weeks e.g., 1 or 2 or 3 or 4 or 5 or 6 weeks, and then administered proton pump inhibitors for up to about 8 weeks e.g., 1 or 2 or 3 or 4 or 5 or 6 or 7 or 8 weeks. The Stage 3 condition may be a Stage 3 cancer, and treatment may continue beyond these time points until Og is eradicated from the patient and, preferably, until the cancer is resolved. Exemplary patients suffering from a Stage 3 condition will be infected with Og but not with Hp, however they may be actively-infected with both Og and Hp.

This invention also provides compositions for preventing the onset and/or the proliferation of diseases and disorders associated with Og infection, such as gastric and non-gastric cancer, via eradication of Og and Hp in patients with Og(+)/Hp(+) co-infection, or Og in patients without Hp infection, Og(+)/Hp(−). For example, the present invention provides a composition comprising a proton pump inhibitor for use as a medicament or in therapy for the treatment or prevention of an Og-associated disease or disorder in a patient e.g., a precancerous condition e.g., Stage 1 condition or Stage 2 condition, or a cancer such as adenocarcinoma or carcinoma e.g., Stage 3 condition, as described according to any example herein. Preferably, the composition further comprises at least one antibiotic e.g., selected from the group consisting of amoxicillin, tetracycline e.g., doxycycline, at least one quinolone, azithromycin and rifampicin. For example, the present invention provides a kit, comprising a therapeutically effective amount of a plurality of antibiotic compounds and proton pump inhibitor compounds, optionally with instructions for use thereof in the eradication or suppression of Og in a patient in need thereof e.g., in accordance with said patient's stage of cancerous disease or disorder. Exemplary combinations of antibiotics and proton pump inhibitors, and instructions for their use, will be apparent from the preceding description of therapeutic regimens.

This invention extends to the manufacture and use of such compositions in the treatment or prevention of Og-associated conditions e.g., a disease or disorder associated with Og(+)/Hp(−) infection or Og(+)/Hp(+) co-infection, such as adenocarcinoma or lymphoma. For example, the kit of the preceding example may be employed to produce a pharmaceutical composition for such treatment or prevention, by admixture of the kit components, optionally with a pharmaceutically-acceptable carrier, diluent or excipient. Such admixture may be in vitro preceding administration of the resulting combination, however it is to be understood that the kit components may be administered as separate tablet, capsules, injectable liquids or other dosage formulations, the only requirement being that they are used sequentially or simultaneously in treatment or prevention of the Og-associated disease or condition. Specific combinations of proton pump inhibitors with specific combinations of antibiotic compounds will be apparent from the preceding description of therapeutic regimens.

In one example, the present invention provides for use of an amount of a proton pump inhibitor or a combination of different proton pump inhibitors in the preparation of a medicament for treatment or prevention of an Og-associated disease or disorder in a patient e.g., a precancerous condition e.g., Stage 1 condition or Stage 2 condition, or a cancer such as adenocarcinoma or carcinoma e.g., Stage 3 condition, as described according to any example hereof. In another example, the present invention provides for use of one or more proton pump inhibitors and at least one antibiotic compound in the preparation of a medicament for treatment or prevention of an *Okadaella gastrococcus*-associated cancer. Preferably, the at least one antibiotic compound is selected from the group consisting of amoxicillin, tetracycline e.g., doxycycline, at least one quinolone, azithromycin and rifampicin.

This invention also provides a method of assessing the risk of developing gastric and non-gastric diseases and disorders associated with Og infection, via detecting the presence of Og in Og(+)/Hp(+) co-infection, or Og in patients without Hp infection, Og(+)/Hp(−), and determining the severity and stage of the infection(s). The severity is assessed by methods well known in the art, such as quantifying the level and location of bacterium within the patient, and by assessing the level of histological changes of the infected tissue. The assessment may focus on Og alone, or both Og and Hp infections, wherein the patient is preferably a human. The method may also include the use of a diagnostic kit to rapidly detect Og infection in a patient; such as a polymerase chain reaction based test with 16s RNA probes and primers for Og.

In one example, the present invention provides a method of diagnosing an Og-associated disease or disorder in a subject in need thereof e.g., a subject suspected or at risk of having a precancerous condition e.g., Stage 1 condition or Stage 2 condition, or a cancer such as adenocarcinoma or carcinoma e.g., Stage 3 condition as described according to any example hereof, said method comprising detecting Og in a sample from the subject, wherein the detection of said Og in the sample is indicative of the Og-associated disease or disorder. The diagnostic method of the present invention is particularly useful for diagnosing a susceptibility or risk for developing a cancer such as adenocarcinoma or lymphoma in a subject, preferably at Stage 1 or Stage 2 of the disease progression, and more preferably in a subject exhibiting one or more symptoms selected from superficial gastritis and/or chronically-inflamed gastric mucosa and/or atrophic gastritis and/or intestinal metaplasia. Preferred means for detecting Og in the sample include one or more of e.g., microscopic analysis to detect Og by morphology or staining, selective amplification of Og DNA or Og RNA, or antibody detection such as by ELISA or immunohistochemical detection. The Og may be detected using such means in at least one body tissue or a body fluid of the subject being tested. Means such as microscopy and antibody-base detection may be employed in vivo. Alternatively, ex vivo detection may be employed such as on a biopsy sample or other specimen provided by the subject. Exemplary body tissues in which Og is detected include e.g., gastric mucosa, intestinal mucosa, gastric ulcer or a vessel or lamina propria thereof, stomach tissue, esophagus, gastroesophageal junction, lymphoid tissue, lymph node, colon, lung, occula adnexa, thyroid, salivary gland, brain, heart, bone, bone marrow, pancreas, liver, gall bladder, breast, overy, uterus, muscle, or neural tissue, or a biopsy of such tissues, Exemplary body fluids in which Og is detected include e.g., blood or fraction thereof comprising erythrocytes, and fluids in connection with any of the foregoing tissues and biopsy samples.

The invention is described more completely with reference to the examples provided herein, and the accompanying drawings, which are included for the purposes of exemplification and without limitation.

DEFINITIONS

"Effective amount": In general, the "effective amount" of pharmaceutical composition refers to the amount necessary to elicit a desired biological response. As will be appreciated by those of ordinary skill in this art, the absolute amount of a composition that is effective against Og may vary depending on such factors as the desired biological endpoint, the agent to be delivered, the target tissue, the route of administration, the patient's weight, size, and age, and the potential for any adverse side effects. Those of ordinary skill in the art will further understand that an "effective amount" may be administered in a single dose, or may be achieved by administration of multiple doses.

"Og": The symbol "Og" refers to *Okadaella gastrococcus* bacterium. A sample of *Okadaella gastrococcus* has been deposited with the National Measurement Institute located at 1/153 Bertie Street, Port Melbourne, Victoria 3207, Australia, under the provisions of the Budapest Treaty n the International Recognition of the Deposit of Microorganisms for ht Purposes of Patent Procedure, on Oct. 27, 2010, and assigned Accession No. V10/022,878. Deposit of the microorganism is not an admission that a sample of the microorganism is required to perform the invention disclosed and/or claimed herein.

"Hp": The symbol "lip" refers to *Helicobacter pylori* bacterium.

"Og(+)/Hp(+)": The symbol "Og(+)/Hp(+)" refers to cases in which the patient is actively infected with both bacterium, Og and Hp.

"Og(+)/Hp(−)". The symbol "Og(+)/Hp(−)" refers to cases in which the patient is actively infected with Og, but is not presently infected with Hp. For example, the patient may have undergone successful Hp eradication therapy, which was not effective in eradicating Og. Alternatively, the symbol refers to situations in which the patient has never been infected with Hp, but is infected with Og.

"Patient": The term patient, as used herein, refers to humans as well as non-human animals. Non-human animals may include mammals (e.g., a rodent, a mouse, a rat, a rabbit, a monkey, a dog, a cat, a primate, or a pig). The exemplifications disclosed in this invention all derive from human patients, and the preferred patient is a human.

DETAILED DESCRIPTION OF THE INVENTION

Figure 1:
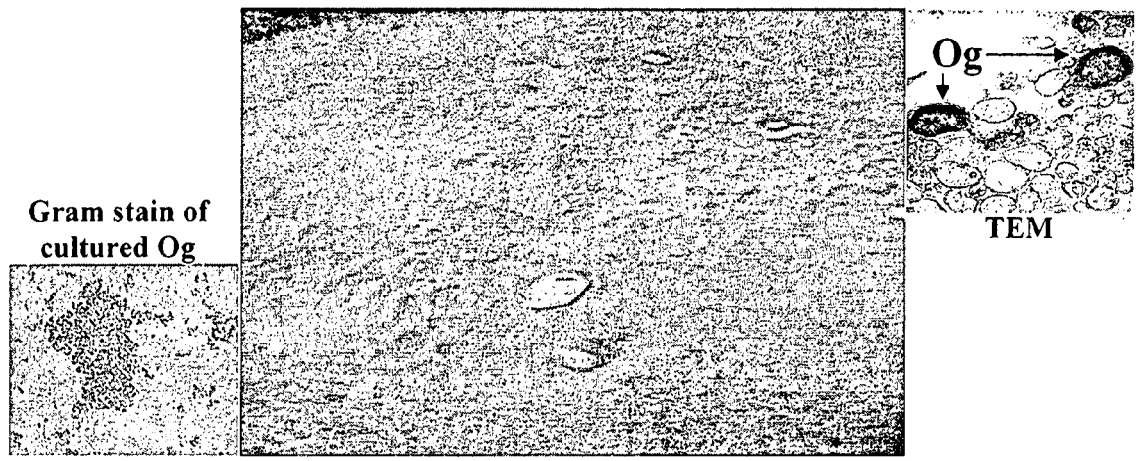
FIG. 1 is an endoscopic image in a case of gastric erosion and ulcer associated with Og infection [Og(+)/Hp(−)]. Gram stained Og which were cultured from the biopsy specimen of the lesion are shown in the lower left corner. Transmission electron microscopy (TEM) of the biopsy specimen from the lesion identified the intracellular presence of Og, which is shown in the upper right corner.

U.S. Pat. No. 6,261,824 teaches that *Okadaella gastrococcus* (Og), a new coccoid form of bacterium which is distinct from *Helicobacter pylori* (Hp), has been associated with dyspeptic symptoms and gastritis in patients. Og was also linked to gastric erosion and ulcers, as demonstrated in FIG. 1, wherein cultured and isolated Og (Gram stained) are shown in the right lower corner. TEM (transmission electron microscopy) of the biopsy specimen from the lesion identified the intracellular presence of Og.

Figure 2:
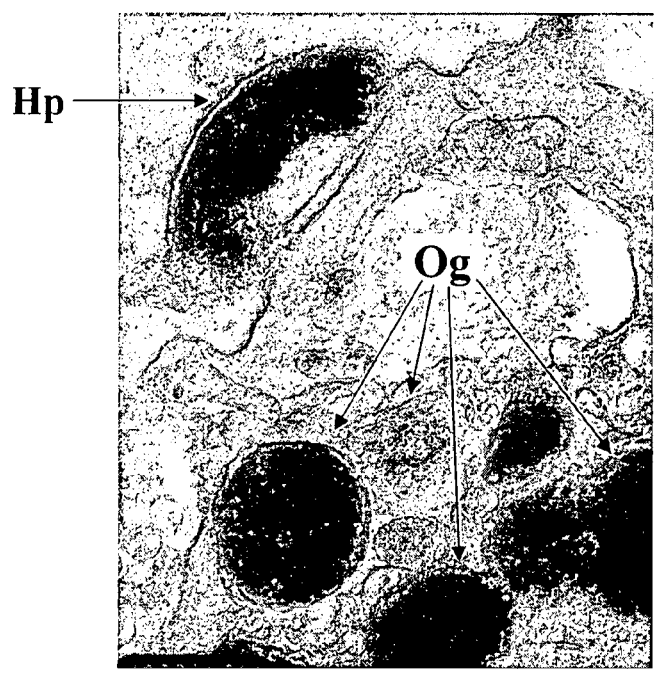
FIG. 2 shows a TEM image of the co-existence of Hp(extracellular) and Og (intracellular) in a patient [Og(+)/Hp(+)].

Og may exist alone or co-exist with Hp in gastric tissue. For example, in FIG. 2 TEM images of gastric tissue in a patient show the co-existence of Hp and Og. While Hp is urease positive; Og is urease, catalase, and oxidase negative, and arginine aminopeptidase and $H_2S$ positive. Hp is normally found intercellularly and on the surface of mucosal epithelial tissue. Og is found intracellularly and intercellularly; on mucosal epithelial tissue, perivascularly, intravascularly, in the lamina propria, and is thus more strongly indicated in systemic infections than is Hp. For example, histology and TEM of the cardiac specimens of a patient who was deceased from myocardial infarction with the occlusion of coronary artery after successful Hp eradication, identified pericarditis and intravascular Og.

The present invention now discloses that Og infection, like Hp, directly correlates to the pathology of Og-associated conditions e.g., gastric and non-gastric cancers. For example, Og, is associated at one or more stages of a disease such as a gastric adenocarcinoma and/or non-gastric adenocarcinoma and/or MALT and/or B cell lymphoma. This invention discloses TEM images generated from biopsies which show the presence of Og with and without the presence of Hp in gastric and non-gastric tissue at various stages of cancer disease pathology. Evidence includes Og involvement in both the onset of gastric and non-gastric adenocarcinomas, as well as MALT and B cell lymphomas.

Gastric Og-Associated Cancer

Figure 3:
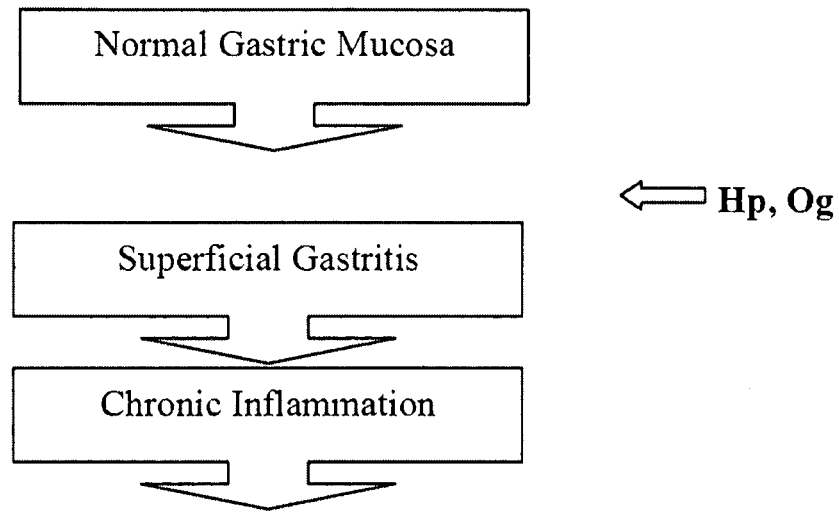
FIG. 3 is a flowchart of the Correa Pathway and the three stages of carcinogenesis for gastric adenocarcinomas.
Figure 3:
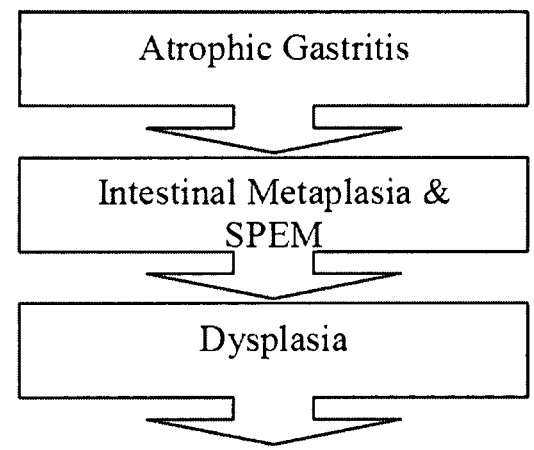
Figure 3:
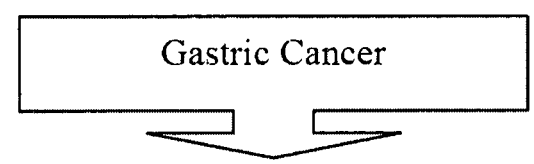

When a patient develops a gastric cancer, they progress through a series of histological changes known as the Correa Pathway (FIG. 3). While most patients are infected in their youth, the process may take decades for the pathology to progress from normal gastric mucosa, to superficial gastritis, to chronic inflammation, to atrophic gastritis, to intestinal metaplasia and spasmolytic polypeptide-expressing metaplasia (SPEM), to dysplasia, and finally onto carcinoma. At the point of gastric atrophy, there is a loss of parietal cells and glandular cells. By the time intestinal metaplasia is reached, a pre-neoplastic state is achieved wherein gastric glands are replaced by an epithelium that histologically resembles the intestinal mucosa. Intestinal metaplasia is divided into three types, I, II, and III. A risk of developing a gastric cancer is generally associated with type III intestinal metaplasia. In rare cases dysplasia follows type III with the appearance of cells that resemble malignant cells seen in full blown gastric cancer.

As exemplified herein, Og(+) infection is detectable in all stages of the Correa Pathway, indicating utility of Og as a target for diagnosis of a predisposition for developing a cancer such as a gastric adenocarcinoma and/or gastric mucosa-associated lymphoid tissue (MALT) lymphoma and/or adenocarcinoma of the gastro-esophageal junction. These findings also demonstrate utility of Og as a therapeutic target in the treatment or prevention of such Og-associated conditions.

Non-Gastric Og-Associated Cancer

Og is more vascularized than Hp, therefore it infects more tissues and organs of the body than Hp, and should thus be linked to more types of non-gastric cancer than Hp. As stated supra, Hp is associated with non-gastric cancers primarily involving mucosal tissues. Og may be involved in systemic diseases including brain, heart, lung, bone and bone marrow, pancreas, liver, gallbladder, breast, thyroid, lymph nodes and lymphatic systems, ovary, uterus, muscle, neural system (nerves), amongst others.

As exemplified herein, Og(+) infection is detectable in non-gastric cancers such as adenocarcinoma of the lung and diffuse large B cell lymphoma, indicating utility of Og as a target for diagnosis of a predisposition for developing a cancer such as a non-gastric adenocarcinoma and/or B cell lymphoma. These findings also demonstrate utility of Og as a therapeutic target in the treatment or prevention of such Og-associated conditions.

Example 1

Case of Gastric Ulcer in Og(+) Patient

Figure 4A:
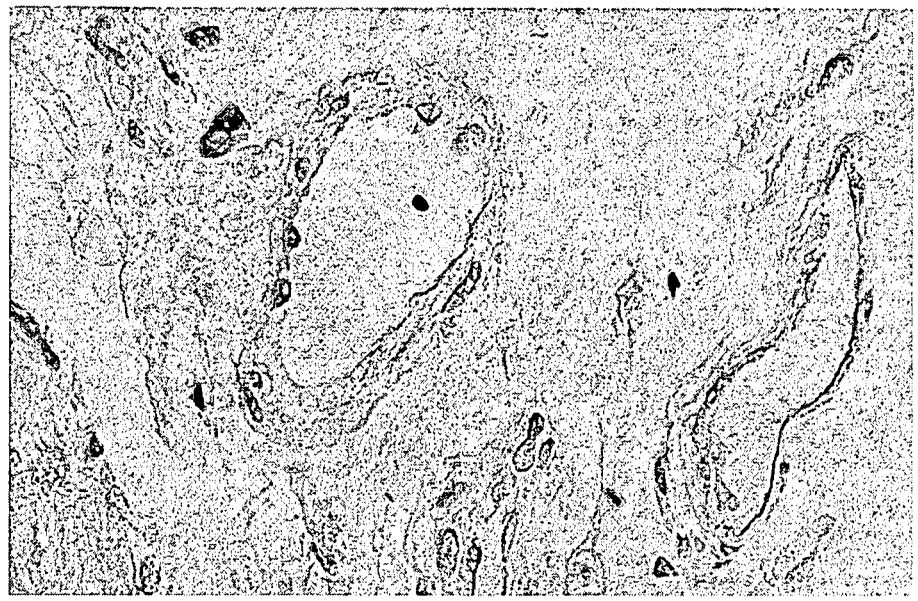
FIG. 4A shows an immunohistochemistry image from a patient with a gastric ulcer which displays the presence of Og, and the absence of Hp, within the blood vessels.

Endoscopic diagnostic procedures were performed on a patient exhibiting symptoms of a gastric ulcer. Immunochemical stains showed the presence of Og, but the absence of Hp in the blood vessels at the site of the gastric ulcer (FIG. 4A).

Figure 4B:
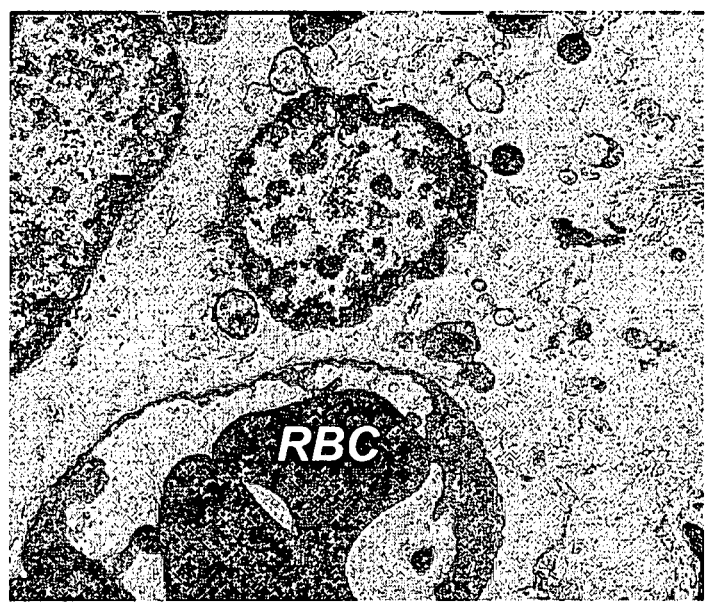
FIG. 4B shows a TEM image of Og (arrows) in the vessel and lamina propria of a gastric ulcer patient. 'RBC' denotes red blood cells.

An endoscopy showed a hemorrhagic gastric ulcer and gastritis in a patient who was a non-NSAID's user. TEM identified the presence of Og (arrows) in the vessel and in lamina propria (×8000) (FIG. 4B). RBC denotes Red Blood Cells.

Example 2

Case of Intestinal Metaplasia and Dysplasia in Og(+) Patient

Figure 5A:
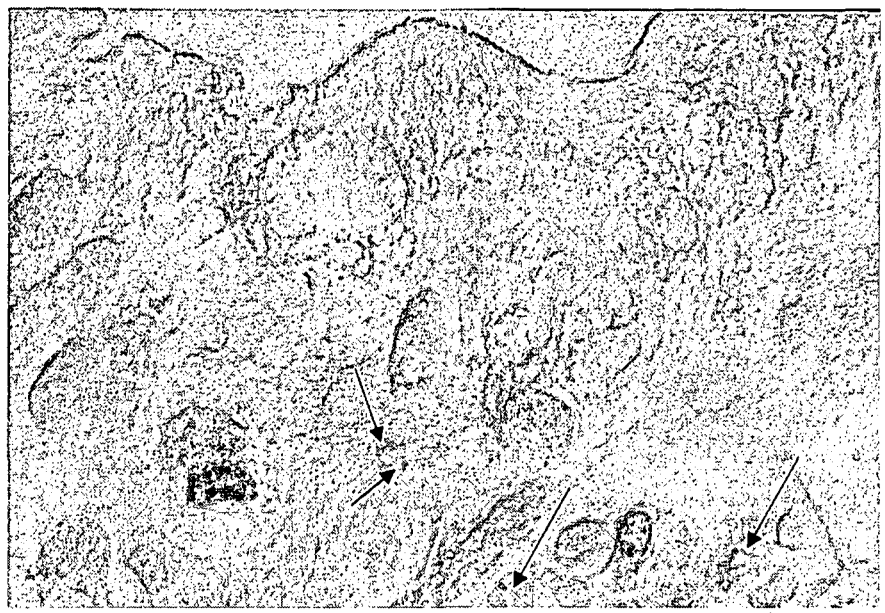
FIG. 5A is an immunohistochemistry image of Og (arrows) identified in a, case of intestinal metaplasia. Og immunoreactivites were found on the cell nuclei and in the cell vessels.
Figure 5B:
FIG. 5B is an immunohistochemistry image of Og (arrows) identified in a case of low grade dysplasia.

From patients with gastrointestinal complaints, Og immunoreactivities (arrows) were seen in an area of intestinal metaplasia (FIG. 5A), and in a case of low grade dysplasia (FIG. 5B).

Example 3

Case of Adenocarcinoma of the Stomach in Og(+) Patient

Figure 6A:
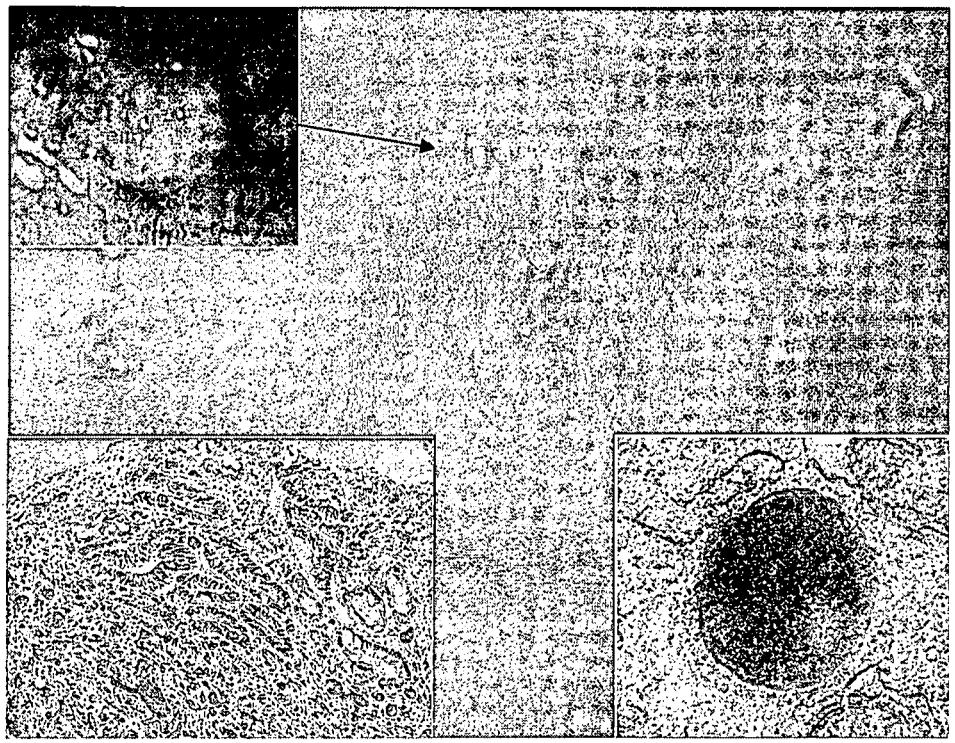
FIG. 6A is an endoscopic image of gastric adenocarcinoma developing in the stomach of a patient after successful eradication of Hp, but persistent infection with Og under TEM.

The patient had active chronic gastritis associated with Hp and Og infection. The patient had a successful Hp eradication that was confirmed with culture, histology, Hp immunochemistry, and electron microscopy. He had persistent Og infection, and thus he had annual endoscopic follow-up examinations. He subsequently developed adenocarcinoma of the stomach 5.5 years after the successful eradication of Hp (FIG. 6A).

Example 4

Case of Adenocarcinoma of GEJ in Og(+) Patient

In industrialized countries, the incidence of Hp has been steadily decreasing, while the incidence of esophageal cancer has been increasing. Some studies have shown that the eradication for Hp in patients with chronic atrophic gastritis reduced both the incidence of gastric adenocarcinoma and esophageal adenocarcinoma, irrespective of the presence of reflux esophagitis or Barrett's esophagus (Mager, D. L., 2006). Og infection is herein linked to adenocarcinoma of the gastro-esophageal junction.

Figure 6B:
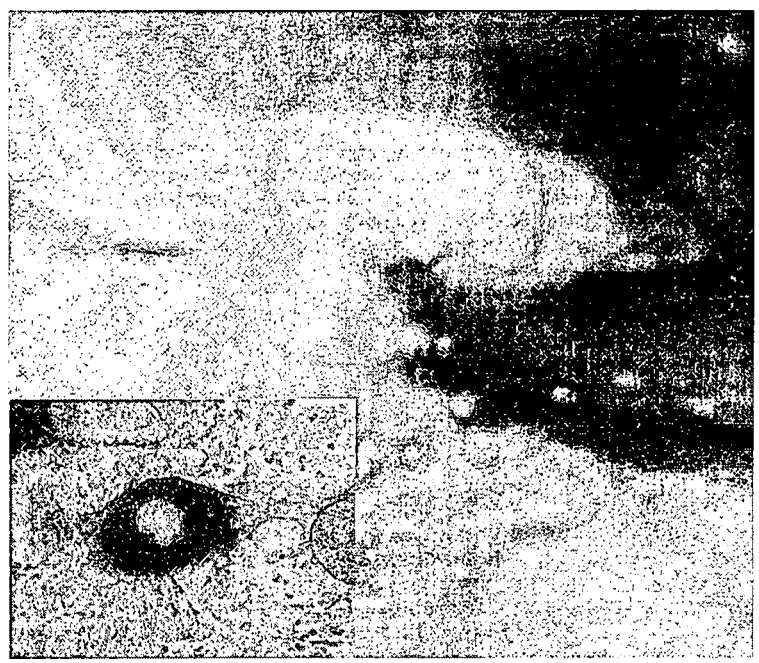
FIG. 6B is a TEM image of a biopsy specimen from an adenocarcinoma of the gastroesophageal junction (GEJ) that shows intracellular Og in the cancer cells.

FIG. 6B is an endoscopic image of a biopsy specimen from a patient with adenocarcinoma of the gastro-esophageal junction (GEJ). TEM of the biopsy specimen shown in the lower left corner of FIG. 6B shows intracellular Og in the cancer cells.

Example 5

Case of Gastric MALT Lymphoma in Og(+) Patient

Extranodal marginal zone B cell lymphomas of mucosa associated lymphoid tissue, otherwise known as MALT lymphomas, are found primarily in the stomach, but also in the colon, lung, occula adnexa, thyroid, and salivary glands. Approximately 5% of gastric tumors are lymphomas, with about 40% being low grade MALT and 60% high grade diffuse large B cell lymphomas (DLBCL). Approximately, 5-10% of gastric MALT lymphomas appear not to be associated with Hp infection, and other bacteria, such as Og, may be the primary causative factor. As shown herein, Og is been found in MALT and B cell lymphomas in the absence of Hp.

Figure 8:
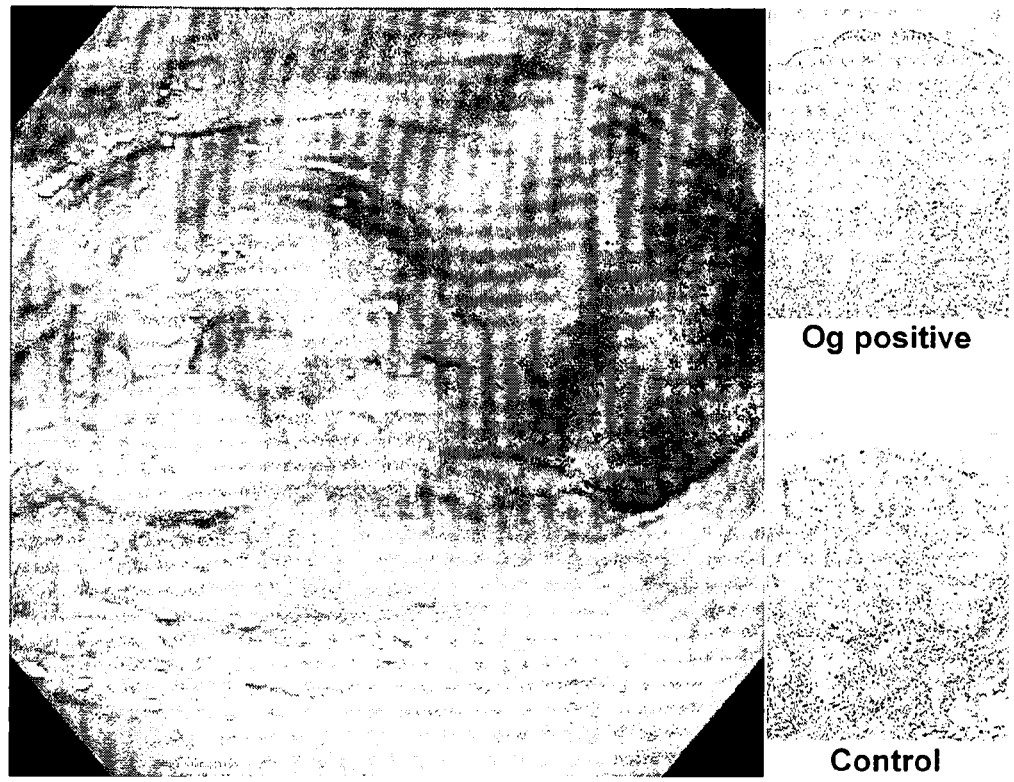
FIG. 8 is an endoscopic image of gastric MALT lymphoma in a patient who was Og positive and Hp negative for immunochemistry.

A patient was diagnosed with gastric MALT lymphoma, as seen in the endoscopic image of FIG. 8. The picture in the right upper corner shows positive Og immunoreactivity (e.g., Og immunohistochemistry) of the biopsy specimen from the lesion. However, Hp immunohistochemistry for the specimen was negative (shown in the right lower corner)

Example 6

Case of Diffuse Large B Cell Lymphoma in Og(+) Patient

Figure 9:
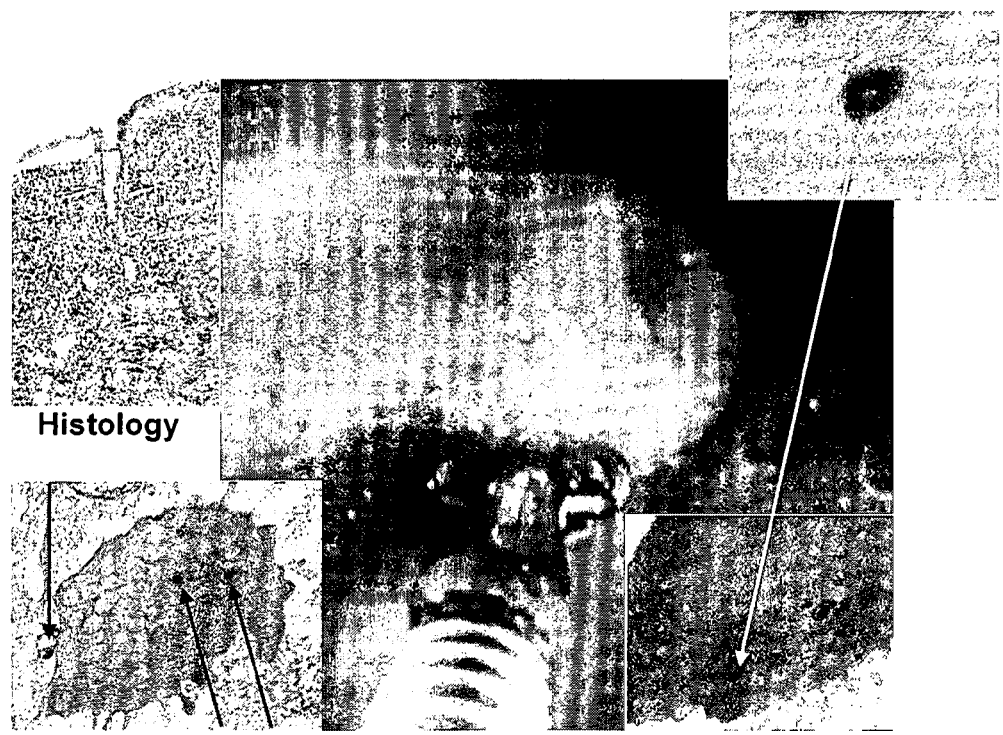
FIG. 9 is an endoscopic image of the biopsy specimen from a patient with diffuse large B cell lymphoma. TEM images of the biopsy specimen identified intracellular presence of Og in the lymphoma cells.

A patient displays a diffuse large B cell lymphoma on endoscopic imaging (FIG. 9). The picture of the left upper corner shows the histology (H&E stain). TEM of the biopsy specimen from the lesion identified the presence of intracellular Og in the lymphoma cells.

Example 7

Case of Adenocarcinoma of Lung in Og(+) Patient

Figure 10:
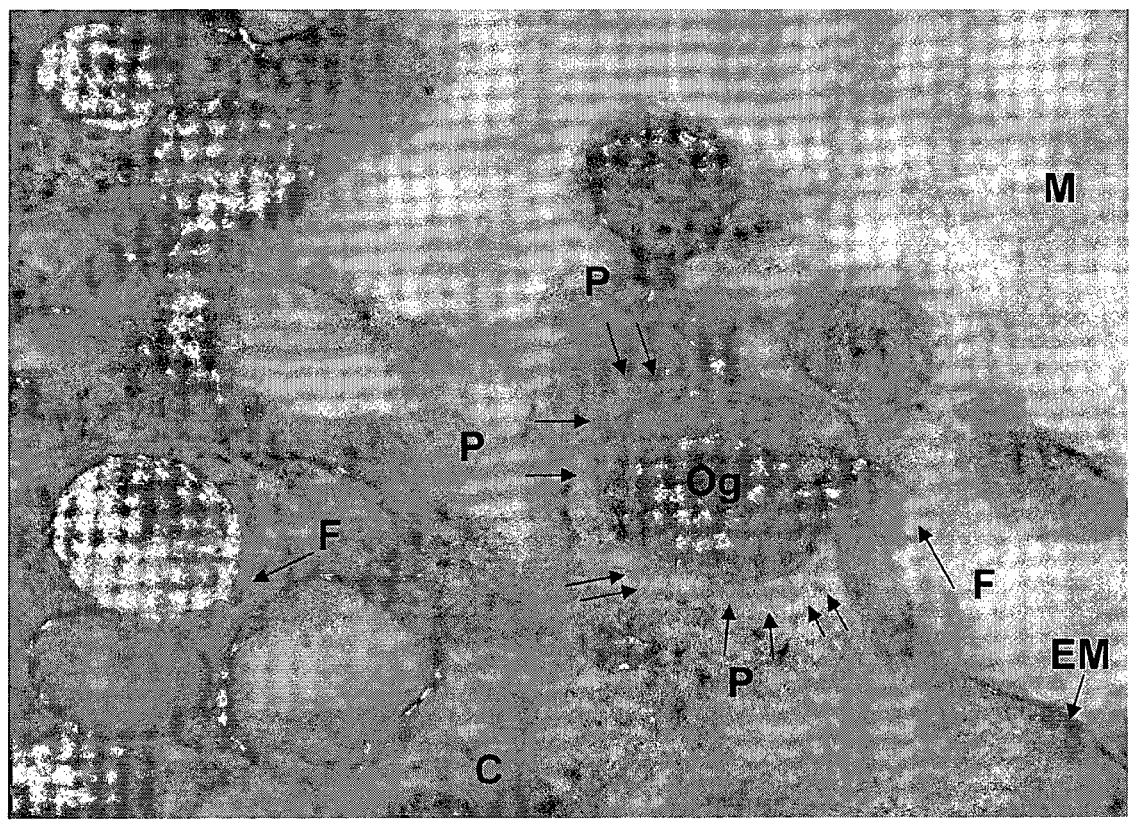
FIG. 10 is a TEM image of a gastric biopsy specimen from a patient with adenocarcinoma of lung showing intracellular Og. Note that in the figure, 'P' denotes pili, 'C' cytoplasm, 'F' flagella, 'M' mucous layer, and 'EM' epithelial cell membrane.

FIG. 10 is a TEM of the gastric biopsy specimen from a patient with adenocarcinoma of the lung. The arrows show directly invading Og and intracellular Og. Multiple pili are shown around the invading Og. Note that in the figure, 'P'

Example 8

Mechanism of Pathogenesis by *Okadaella gastrococcus*

The development of gastric adenocarcinomas are generally believed to be the result of alterations in DNA caused by chronic inflammation, recruitment and engraftment of bone marrow-derived stem cells, an imbalance between epithelial cell proliferation and apoptosis, and gastric colonization by enteric bacteria and their production of toxins that disturb the cell cycle resulting in altered cell growth and apoptosis of normal cells.

Particular strains of Hp are believed to be especially virulent via altered gene expressions in babA2, cagA, and vacAS1. About 10% of Hp can adhere to gastric epithelial cells using bacterial cell-surface receptors, such as Lewis B-binding adhesion BabA. Additionally, strains of Hp containing a functional cag locus, which is a 40 kb DNA region that encodes a type IV secretion system responsible for translocating cagA into gastric epithelial cells, causes morphological derangement of epithelial cells. Cag locus has also been associated with the induction of epithelial cells to produce proinflammatory modulators such as IL-8. This Hp strain also induces a proinflammatory response when epithelial cells detect the presence of Hp peptidoglycan protein within the cell which triggers the production of the proinflammatory chemokines IL-8 and CXC-chemokine ligand 2, and the antimicrobial peptide hBD-2. Additionally, strains of Hp expressing vacuolating cytotoxin VacA, block proliferation of T cells proliferation thus contributing to the persistence of Hp infection. (Fox et al, 2007)

Chronic inflammation in gastric tissue, as seen in Og and/or Hp infections, has also been shown in various studies to result in the recruitment of bone marrow-derived endothelial progenitors, bone marrow-derived myofibroblasts, and bone marrow-derived epithelial cells into the gastric tissue. The exact mechanism as to how this occurs is unclear but it appears to involve macrophages and Th1 lymphocytes responding to the bacterial infection, e.g. Hp, which results in increased cytokine and chemokine production (IL-6, IL-1 beta, TNF-alpha, IFN-gamma, and CXCL 12). Recruited bone marrow derived stem cells have been isolated in cases of metaplasia, dysplasia, and cancer associated with Hp infection, which were preceded by severe chronic inflammation.

Hp induced chronic inflammation has also been shown to cause the generation of reactive oxygen species and increasing levels of nitric oxide synthase. This results in mutations by deamination of DNA, and the activation of DNA methyltransferases leads to gene silencing by methylation of promoters containing CpG islands. The condition also promotes apoptosis of normal cells, which increases epithelial cells proliferation as a compensatory response of the remaining tissue.

Figure 7:
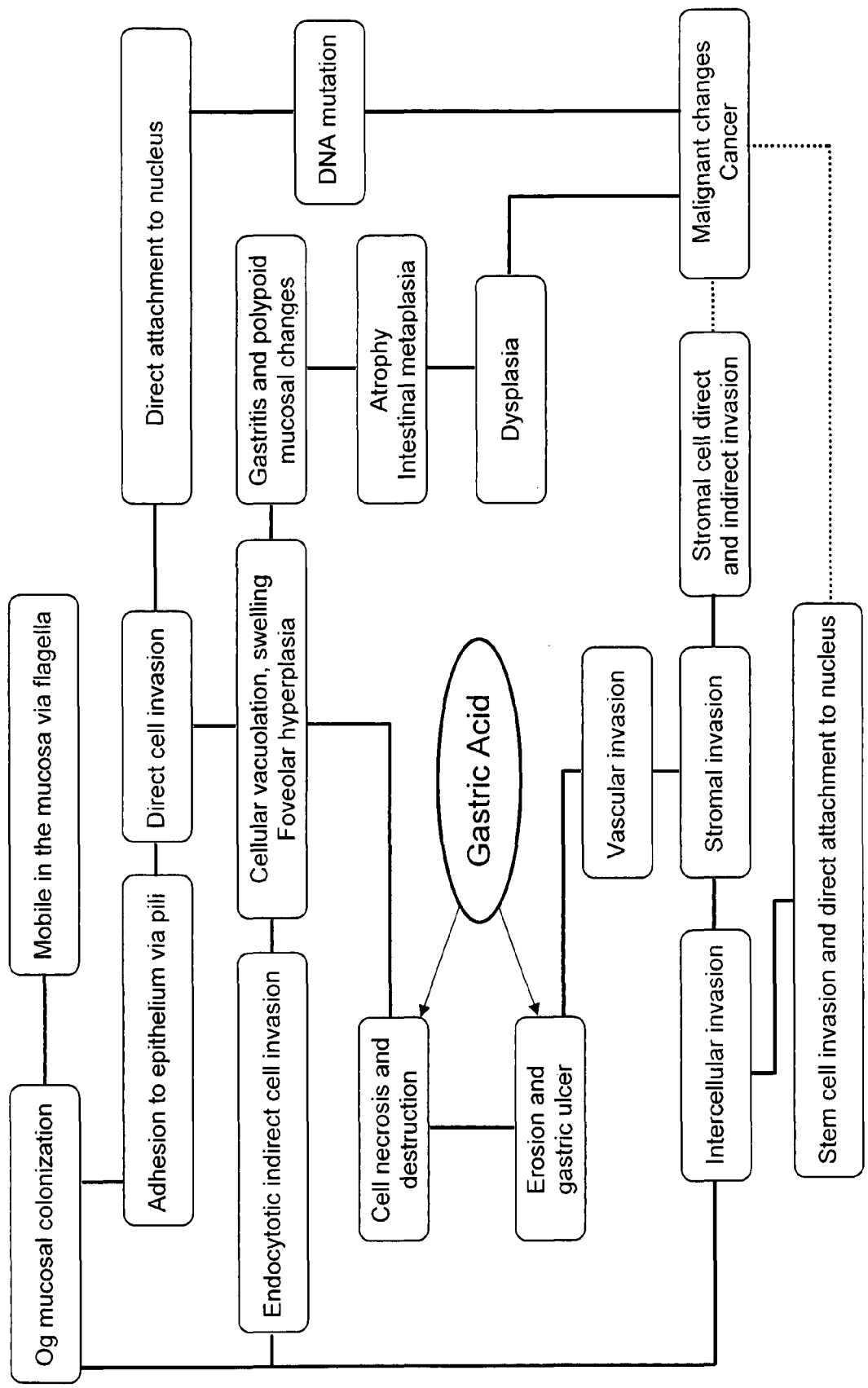
FIG. 7 is a schematic diagram outlining the "Pathogenic mechanism of gastric mucosal lesions induced by *Okadaella gastrococcus* infection".

Although Og displays pathogenic, mechanisms comparable to Hp, such as elicitation of chronic inflammation, there are notable differences. (See FIG. 7).

While not being bound by theory, some of the mechanisms and virulent factors by which Og is believed to be a causative factor in gastric cancer development include: the ability to colonize the stomach lining; the ability, to reduce sulfate to hydrogen sulfide; the production of arginine aminopeptidase, a proteolytic enzyme; the ability to reside intracellularly and attach to the nucleus; and the production of toxins that disturb the cell cycle resulting in altered cell growth. $H_2S$ production of Og at cytoplasmic membrane coupling with an electron-transport system of sulfate-reducing bacteria generates $HCO_3^-$, which provides the survival mechanisms in the gastric acidic condition.

Og is a flagellate bacterium which has demonstrated more mobility than Hp. While Hp is normally isolated to the top layer of the mucosal tissue, Og uses it flagella to propel itself into mucosal tissue to the lamina propria, as well as perivascularly and intravascularly. Its high motility results in increased bacterial colonization of the stomach, followed by chronic gastritis leading to dysplasia and cancer. Colonization may also be enhanced by the proteolytic enzyme activity demonstrated via Og's production of arginine aminopeptidase.

And like other Gram-negative bacteria, the outer membrane of Og is comprised of lipopolysaccharide (LPS). The protein may be fucosylated in a manner similar to Hp such that is mimics Lewis blood group antigens, aiding molecular mimicry of host antigens and the associated immune system evasion. LPS containing bacteria have also displayed phase variation contributing to population heterogeneity and the adaptation of the bacteria to changing conditions in the gastric mucosa, thus prolonging its survival.

In vitro assays have demonstrated that Og is a sulfate-reducing bacteria, thereby producing hydrogen sulfide ($H_2S$), which has been linked in epidemiologically studies to inflammatory bowel disease (such as ulcerative colitis) and colorectal cancer. It has been suggested that sulfide, through its toxic properties, damages epithelium, thereby inciting inflammation. Other studies have demonstrated that $H_2S$ may perturb the balance between apoptosis, proliferation, and differentiation in intestinal epithelial cells. It has also been recently shown that $H_2S$ is capable of generating DNA damage that may in part be responsible for the generation of the genomic instability and the cumulative mutations found in adenomatous polyps leading to colorectal cancer (Attene-Ramos et al, 2006). And it has been established that $H_2S$ stimulates the Ras/Raf/MEK/ERK kinase pathway, thus promoting cell division and colorectal tumorigenesis (Huycke et al, 204).

While Hp is found intercellularly, Og is found intercellularly and intracellularly. In vitro assays have also demonstrated the ability of Og to attach to the nuclear cell membrane of HeLa cells. The intracellular invasion can result in DNA damage and mutation, as well as cell damage and destruction. In an in vitro assay with Vero cells, Og induced hummingbird phenomenon, which is characterized by the elongation of Vero cells under cytotoxic effects of Og.

Method of Preventing Gastric Adenocarcinomas—the Point-of-No-Return Theory

For both adenocarcinomas and lymphomas associated with bacterial infections, the current established methods of prevention and treatment are based on a "Point-of-No-Return Theory". As shown in the Correa Pathway supra, when a patient develops gastric atrophy, which is defined as the loss of specialized glandular tissue and parietal cells, then they have reached "the point-of-no-return", wherein bacterial eradication alone is not sufficient therapy to prevent the onset of adenocarcinomas (Prinz et al, 2006) The loss of parietal cells is associated with a reduction in secreted signals that modulate growth and differentiation of gastric progenitors. This is believed to further lead to an increase in proliferation and accumulation of undifferentiated progenitors, which directly contributes to tumor formation (Fox et al, 2007). It has also been shown that at the intestinal metaplasia stage, a number of molecular alterations can occur that may condemn the fate of the tissue to tumorgenesis: altered transcription factors CDX1 and CDX2, telomerases, microstability, mutations of the p53 protein, overexpression of COX-2, cyclin D2, and decreased expression of p27. Then during gastric dysplasia, the combination of mutations in genes, such as p53, loss of heterozygosity of the adenomatous polyposis coli gene, and overexpression of the antiapoptotic gene bcl-2, results in malignant cell formation (Leedham et al, 2005).

The "point-of-no-return" gastric cancer prevention protocol has repeatedly been demonstrated in human clinical trials. For example, trials in China and Japan have shown that bacterial eradication therapy, e.g. for Hp, in patients who have not progressed to atrophy, resulted in zero incidence of gastric cancer in long term studies. But, patients with atrophy or intestinal metaplasia at the time of treatment showed no regression and had an increased incidence of progressing to cancer (Prinz et al, 2006). There are other studies that show, though, that gastric atrophy may be reversible in time (5-10 years) if treated appropriately (Toyokawa et al, 2009) Additionally, in an animal model of Hp induced gastric cancer, Hp eradication at the atrophy stage resulted in a significantly lower incidence of gastric cancer, while Hp eradication at the intestinal metaplasia and dysplasia stage substantially prevented progression to highgrade gastrointestinal intraepithelial neoplasia (GIN) but not to low grade GIN (Lee et al, 2008).

Method of Prevention and Regression of Lymphomas—The Point-of-No-Return Theory

Gastric lymphomas are categorized according to the extent of tumor invasion into the gastric wall and the involvement of regional lymph nodes (See Table 1 below for definition of the stages of lymphomas) (Du et al, 2006). One predictive factor in assessing the efficacy in bacterial eradication leading to tumor regression is the depth of parietal infiltration. In one recent study, Hp eradication resulted in complete tumor regression in 78% of the cases involving infection of only the mucosa, 43% for the submucosa, 20% for the muscularis, and 25% for the serosa. (Ruskone-Fourmestraux et al, 2001). Another predictive factor is whether the lymphomas have spread to the lymph nodes. Stage $II_E$ through Stage $IV_E$ gastric lymphomas, which involve lymph nodes, have been shown to not be as responsive to Hp antibiotic treatments administered alone. The stages therefore represent the "point-of-no-return", such that chemotherapy and radiotherapy are required in addition to bacterial eradication, while surgical resection is not recommended because of the diffuse spreading of the tumors within the mucosa.

TABLE 1

Staging System for Primary Gastric Lymphomas

| | |
|---|---|
| $I_E$ | Localized disease- no lymph node involvement |
| $I_{E1}$ | Confined to mucosa and submucosa |
| $I_{E2}$ | Extending beyond the submucosa and into muscularis propria |
| $II_E$* | Localized disease with lymph node involvement |
| $II_{E1}$ | Regional lymph nodes involved |
| $II_{E2}$ | Infiltration of lymph nodes beyond regional areas |
| $III_E$ | Localized disease, lymph nodes involved on both sides of diaphragm. |
| $IV_E$ | Diffuse or disseminate involvement of non-GI tract organs |

*Point-of-No-Return- for administering bacterial eradication therapy to cause lymphoma regression.

Example 9

Prevention and Treatment of *Okadaella gastrococcus*-Associated Cancer

This invention discloses the utility of proton pump inhibitors and, optionally, antibiotic therapy are effective in eradicating Og in patients at various stages of pathology.

In Vitro Antibiotic Sensitivity of Og

In vitro assays have demonstrated that Og can be treated using various antibiotics, to include, for example: ampicillin, cefotaxime, ciprofloxacin, gatifloxacin, moxifloxacin, and chloramphenicol Methodology: Gastric specimens from Og (+) patients were cultured under microaerophilic and anaerobic condition at 37° C. with chocolate agar containing 10 mg/l vancomycin over 4-14 days. Twenty-five Og isolates were obtained from gastric mucosal biopsy specimens. E-tests and diffusion disc tests were performed under microaerophilic condition (Oxygen 5%, $CO_2$ 10%, and Nitrogen 85%) utilizing. 5% horse blood agar, except metronidazole which was tested under anaerobic condition. Antibiotic sensitivity was read 72 hours after incubation. Randomly selected isolates were also examined under TEM to confirm the ultrastructure of Og. Results: Og was sensitive to various antibiotics, in particular to the penicillins, the cephalosporins, the quinolones, and chloramphenicol.

Composition Protocol Per Stage of Pathology in Hp and Og Co-Infections:

The stage of Og induced diseases and disorders plays a large determinate in selecting the correct composition treatment protocol to administer to a patient so as to prevent, or delay the onset of, or reduce the severity of Og induced cancer and diseases. For example, the more progressive a gastric lesion is to developing into cancer, the longer the anti-Og compositions are administered and at a higher doses. Exemplifications for treating Stage 1, 2, and 3 adenocarcinomas and lymphomas, as developed from in vivo data by the inventor of this invention from treating human patients infected with Og, are disclosed in Table 2.

As per Table 2, treatment for Stage 1, 2, or 3 adenocarcinomas or lymphomas with either Program A or B, the following drug substitutes and doses may be appropriate for use in this invention. Tetracycline derivatives well known in the art are: Tetracycline, Oxytetracycline, Doxycycline, or Minocycline. Azithromycin, and Rifampicin may be substituted for Quinolones or Tetracyclines depending on the sensitivity of Og and response of the pathology. PPI's well known in the art are: Omeprazole, Lansoprazole, Rabeprazole, Pantoprazole, Esomeprazole, and Zegarid. And Quinolone type drugs with dosing examples includes: Ciprofloxacin (1 g/day in divided dose), Gatifloxacin (400 mg/day), Sitafloxacin (400 mg/day), Sprafloxacin (400 mg/day), Moxifloxacin (400 mg/day), and Levofloxacin (500 mg-1.0 g/day).

TABLE 2

Og Eradication Protocol for Gastric & Non-Gastric* Og Associated Cancers

| Stage | Adenocarcinoma | Lymphomas | Program | Og(+)/Hp(+); Og(+)/Hp(−)** |
|---|---|---|---|---|
| | Non-neoplastic: | | | |
| 1 | Normal Mucosa Super. Gastritis Chronic Inflam. | Stage $I_E$, $I_{E1}$, $I_{E2}$ | A | 2 weeks: Tetracycline, Amoxicillin, PPI<br>4 weeks: Quinolones, Amoxicillin, PPI<br>4 weeks: PPI (2×/day)<br>4 weeks: PPI (1×/day) |
| | | | or B | 4 weeks: Tetracycline, Quinolones, PPI<br>4 weeks: PPI (2×/day)<br>4 weeks: PPI (1×/day) |
| | Pre-neoplastic: | | | |
| 2 | Atrophy Intest. Metaplasia Dysplasia | Stage $I_E$, $I_{E1}$, $I_{E2}$ | A | 2 weeks: Tetracycline, Amoxicillin, PPI<br>4 weeks: Quinolones, Amoxicillin, PPI<br>4 weeks: PPI (2×/day)<br>4 weeks: PPI (1×/day) |
| | | | or B | 6 weeks: Tetracyclines, Quinolones, PPI<br>4 weeks: PPI (2×/day)<br>4 weeks: PPI (1×/day) |
| 3 | Cancer | Stage $II_E$, $II_{E1}$, $II_{E2}$, $III_E$, $IV_E$ | A or B and | Same as Stage 2, A or B,<br>Tetracycline or Doxycycline, Quinolones, & PPI until cancer resolves*** |

*These protocols apply to non-gastric Og associated diseases and disorders wherein the "Stage" of the disorder within the affected tissue or organ indicates the protocol to administer.
**Alternatively at Stage 1, 2 or 3, the patient is administered Azithromycin, Rifampicin instead of Quinolones or Tetracyclines depending on the sensitivity of Og and response of the pathology
***The patient can be treated simultaneously by surgical or oncological intervention under the therapy.

Adenocarcinoma, Stage 1:

As shown in Table 2, for patients infected with Og(+)/Hp(+) or Og(+)/Hp(−) who are at the non-neoplastic Stage 1 of adenocarcinomas, Program A or Program B drug protocol is administered. Program A comprises administering a two week course of triple combination therapy comprising: a Tetracycline derivative (at 1.5 g in divided dose), Amoxicillin (at 3 g/day in divided dose), and proton pump inhibitors (PPIs) (once in the morning and at night). This two week course is then followed by a four week course of triple combination therapy comprising: Quinolones, Amoxicillin (at 3 g/day in divided dose), and proton pump inhibitors (PPIs) (once in the morning and at night). In lieu of the six week Program A schedule, the patient may be administered Program B—a four week course of triple therapy comprising: Tetracyclines (1.5 g in divided dose) or Doxycycline (200 mg/day), Quinolones, and proton pump inhibitors (once in the morning and once at night). Both Program A and B are followed by an eight week course of proton pump inhibitors: once in the morning and at night for four weeks, then one time per day for four weeks.

Stage 2:

If the patient is at pre-neoplastic Stage 2 of adenocarcinoma pathology, then the same treatment as Stage 1, Program A may be administered: a two week course of triple combination therapy comprising a Tetracycline derivative (at 1.5 g in divided dose), Amoxicillin (at 3 g/day in divided dose), and proton pump inhibitors (PPIs) (once in the morning and at night). This two week course is then followed by a four week course of triple combination therapy comprising: Quinolones, Amoxicillin (at 3 g/day in divided dose), and proton pump inhibitors (PPIs) (once in the morning and at night). Alternatively, the same treatment as Stage 1, Program B may be administered wherein the length of the protocol is extended from four weeks to six weeks: triple combination therapy comprising Tetracyclines (1.5 g in divided dose) or Doxycycline (200 mg/day), Quinolones, and proton pump inhibitors (once in the morning and once at night). Both protocols for Stage 2 may be followed by an eight week course of proton pump inhibitors: once in the morning and at night for four weeks, then one time per day for four weeks.

Stage 3:

And if the patient is at an advanced Stage 3 of Og induced adenocarcinoma pathology, then the same treatment as Stage 2, Program A or B is administered, followed by continuous triple combination therapy comprising: Tetracyclines (1.5 g in divided dose) or Doxycycline (200 mg/day), Quinolones, and proton pump inhibitors (once in the morning and once at night) until the cancer resolves. If the patient does not wish to undergo active therapy, then he may be treated conservatively with proton pump inhibitors (once in the morning and at night) or once daily. Additionally, the patient can be treated with triple combination drug therapy, or proton pump inhibitor therapy while undergoing surgical or oncological intervention appropriate for the treatment of the cancer.

Lymphomas:

Likewise, for patients infected with Og(+)/Hp(+) or Og(+)/Hp(−) who are at Stage 1 or 2 of lymphoma pathology, e.g. Stage $I_E$, $I_{E1}$, or $I_{E2}$, as per Table 1, the following Program A or B protocol is administered (see Table 2). As per Program A—a two weeks course of triple combination therapy comprising: Amoxicillin (at 3 g/day in divided dose), Tetracycline derivative (at 1.5 g in divided dose), and proton pump inhibitors (PPIs) (once in the morning and at night). This is followed by a four week course of triple combination therapy comprising: Amoxicillin (at 3 g/day in divided dose), proton pump inhibitors (once in morning and at night), and Quinolones. Again, dosage examples of Quinolones includes: Ciprofloxacin (1 g/day in divided dose), Gatifloxacin (400 mg/day), Sitafloxacin (400 mg/day), Sprafloxacin (400 mg/day), Moxifloxacin (400 mg/day), Levofloxacin (500 mg-1.0 g/day). In lieu of the six weeks Program A schedule, the patient may be administered Program B—a four or six weeks course of triple therapy comprising: Tetracyclines (1.5 g in divided dose) or Doxycycline (200 mg/day), Quinolones, and proton pump inhibitors (once in the morning and once at night). Optionally, both Program A and B are followed by an eight week course of proton pump inhibitors: once in the morning and at night for four weeks, then one time per day for four weeks. And if the patient is at Stage 3, an advanced stage of Og induced lymphoma pathology which has historically shown to be unresponsive to bacterial eradication therapy alone, e.g., Stage $II_E$, $II_{E1}$, $II_{E2}$, $III_E$, or $IV_E$, then the same therapy as Stage 2, Program A or B, can be administered followed by continuous triple combination therapy comprising: Tetracyclines (1.5 g in divided dose) or Doxycycline (200 mg/day), proton pump inhibitors (once in the morning and at night), and Quinolones until the cancer resolves. If the patient does not wish to undergo active therapy, then he may be treated conservatively with proton pump inhibitors (once in the morning and at night) or once daily. Additionally, the patient can be treated with triple combination drug therapy, or proton pump inhibitor therapy while undergoing surgical or oncological intervention appropriate for the treatment of lymphomas.

Alternative Treatment Protocol in Og(+)/Hp(−) Infections:

Alternatively, for patients infected with Og alone, in the absence of Hp, the method of treatment for non-neoplastic stage (Stage 1), pre-neoplastic stage (Stage 2) and advanced stage (Stage 3) adenocarcinomas or lymphomas are the same for all three stages. The patient is administered triple combination therapy for four weeks (Stage 1) to six weeks (Stage 2 and 3) comprising: Quinolones, the types and doses as disclosed supra, Tetracyclines derivatives (at 1.5 g in divided dose), and proton pump inhibitors (once in morning and at night). This may then followed by eight weeks of proton pump inhibitors (2 times/day for 4 weeks, and 1/day for 4 weeks).

For both Og(+)/Hp(+) and Og(+)/Hp(−) infections, complete bacterial eradication is not required to prevent the development of associated diseases, e.g. cancer. Either reduction of the amount of Og/Hp, or altering of the immune response, should result in a significant decrease in inflammation, thus reducing the induction of associated diseases and disorders.

Bacterial Resistance:

In cases of both co-infection with Hp and Og, or infections with Og alone, there is the possibility that the patient may exhibit a resistance to one of the administered antibiotics, in which case a substitution should be made with another antibiotic well known in the art as an efficacious alternative. For example, should the patient with Og infection display a resistance to Quinolones or Tetracyclines, then it may be replaced with Rifampicin or Azithromycin at a comparable dose well known by one of ordinary skill in the art.

Probiotics:

Additionally, for both Og(+)/Hp(+) and Og(+)/Hk(−) patients in Stage 1 and Stage 2, a probiotic treatment protocol may be commenced and administered in the third and fourth week of treatment. It should be continued for 4 weeks of post-Og eradication period. Probiotics prevent further infection with pathogenic bacteria both through activation of the host's immune system and through direct competition of the probiotic bacteria with the pathogen. Lactic acid bacteria (LAB), and bifidobacteria are the most common types of microbes used as probiotics. Other probiotics with demonstrated efficacious against Hp may be administered, and by way of exemplification may include: *Lactobacillus rhamnosus* GG, *Lactobacillus rhamnosus* Lc705, *Propionibacterium freudenreichii* subsp. *shermanii* Js, and *Bifidobacterium breve* Bb99.

It should also be noted that methods of preventing the development and progression of all cancers and other disorders due to infection by Og throughout a patient's body is not limited to the above disclosed compositions comprising a proton pump inhibitor alone or alternatively with at least one antibiotic. Rather, Og infections may be treated with any composition shown to eradicate Og, or similar bacterial infection, such as Hp. One of ordinary skill will appreciate that effective amounts of the compositions and anti-infective agents of the invention can be determined empirically and can be employed in pure form or, where such forms exist, in pharmaceutically acceptable salt; ester or procomposition form. The agents can be administered to a patient, in need of treatment of an Og infection, as pharmaceutical compositions in combination with one, or more pharmaceutically acceptable excipients. It will be understood that, when administered to a human patient, the total daily usage of the agents or composition of the present invention will be decided by the attending physician within the scope of sound medical judgment. The specific therapeutically effective amount, or dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration (e.g., oral, injection-intravenous, intramuscular, intradermal), and rate of excretion of the agent; the duration of the treatment; compositions used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

Combination Therapy:

There is also growing evidence that intestinal metaplasia due to bacterial infection, such has Og(+) and/or Hp(+), may be reversible if used in conjunction with other anti-cancer therapies. In an Italian study, co-administration of ascorbic acid, i.e., Vitamin C, with Hp eradication therapy significantly resolved the intestinal metaplasia of the gastric mucosa. And a study in Columbia showed that dietary supplementation with antioxidant micronutrients along with Hp eradication therapy significantly increased the rate of regression of cancer precursor lesions in patients with intestinal metaplasia (Walker, M. W., 2003). Intestinal metaplasia has also been characterized as the overexpression of cyclooxygenase-2 (COX-2), which is concomitant with an increase in cell proliferation and angiogenesis. A study administering Celecoxib, which is a selective COX-2 inhibitor, after Hp eradication therapy resulted in a significant improvement in precancerous lesions (Zhang et al, 2009). Similar results were shown in a study administering esomeprazole for reflux esophagitis in patients who had undergone Hp eradication therapy at the intestinal metaplasia stage (Yang et al, 2009).

Adenocarcinoma Combination Protocols:

In cases where the stage of infection is prior to the onset of gastric atrophy, Og and Hp eradication therapy for Stage 1 infection as disclosed supra is the primary treatment for the prevention of gastric cancer. For Stage 2 patients, Og and Hp eradication therapy alone, or in combination with other anti-cancer therapies well known in the art is recommended for patients with gastric atrophy, intestinal metaplasia or dysplasia. At a minimum, these patients should be administered Og and Hp eradication therapy as a baseline therapy.

This therapy may be administered in conjunction with additional short and long-term therapies directed to deficiencies and disorders (genetic, dietary, etc. . . . ) in the patient that have been shown to correlate with the development of carcinomas, and which are well known in the art. The preferred route of administration is oral, although other routes well known by one of ordinary skill in the art may be utilized. And for patients in Stage 3 who have active gastric and non-gastric cancer associated with Og infection, then the patent should be administered Og and Hp eradication therapy, in conjunction with anti-neoplastic agents, that are intended to reduce the size of the primary tumor, to reduce the size of a secondary tumor, to reduce the number of metastases, to reduce the growth rate of a tumor, to reduce the ability of the primary tumor to metastasize, to increase life expectancy, etc.

Approximately one to two months after treatment for any of the above stated Stage 1, 2 or 3 cases, the patient should be re-tested for bacterial eradication. For example, in Og(+)/Hp(+) cases, a urea breath test can be utilized to detect Hp eradication, and TEM imaging for Og eradication. Additionally, in Og(+)/Hp(−) and Og(+)/Hp(+) diagnostic tests for Og may be utilized comprising, for example, rapid detection methods utilizing PCR and reverse transcriptase probes for 16S rRNA and DNA sequences for arginine aminopeptidase. (See U.S. Pat. No. 6,261,824 for additional methods of detection of Og in a patient.) If either bacterial strain exists, then other anti-infective therapy options should be considered in light of the potential for bacterial resistance.

Lymphoma Combination Protocols:

Cases of Og(+)/Hp(+) co-infection, or Og(+)/Hp(−) infection, in a patient diagnosed with at any stage of lymphoma may be administered Og eradication treatment as per Table 2 in combination with other known in the art that is specific to the type and stage of the lymphoma. For example, Og eradication therapy in conjunction with: therapy correcting genetic deficiencies that contribute to the development of lymphomas; or the use of chemotherapy and radiotherapy in Stage $II_E$, $II_{E1}$, $II_{E2}$, $II_{E1}$, or $IV_E$ lymphomas, is appropriate. Approximately one to two months after treatment, the patient should be re-tested for Og and Hp eradication and the possibility of bacterial resistance. Upon evidence of bacterial eradication via non-invasive tests, the patient should eventually undergo an endoscopic procedure and biopsy to assess the regression of the lymphoma.

Treatment and Prevention of Non-Gastrointestinal Carcinoma

The method of prophylactic treatment for the prevention of non-gastric cancer in patients verified for co-infection of Hp and Og, or Og without Hp, comprises administering standard composition protocol for Og and Hg eradication during or prior to the onset of chronic inflammation of the infected tissue or organ using Stage 1 or 2 composition protocol as disclosed supra, e.g. Table 2. Should the patient be in Stage 3, then the appropriate composition protocol is administered, as well as methods of treatment well established in the art for treating cancers of the particular affected tissue or organ.

The route of administration and dose is in accordance with the tissue location and type as known by one of ordinary skill in the art. For example, for patients who have tested positive for Og(+)/Hp(−) or Og(+)/Hp(+) lung tissue infection pre-cancerous, the composition treatment protocol exhibited in Table 2, Stage 2 would be administered. No sooner than one month post treatment should the patient be re-tested for the presence of Hp and Og in patient. If either infection persists, alternative anti-infective treatment protocols should be administered.

Therapeutic Kit

Likewise, the invention encompasses a therapeutic kit and a method of manufacturing a medicament, comprising the use of pharmaceutical compositions for the suppression or eradication of cases involving Og(+)/Hp(−) and Og(+)/Hp(+) in a patient. The kit includes antibiotics, as disclosed for example in Table 2, as well as proton pump inhibitors. The quantity of the compounds within the kit is sufficient a full course of treatment for Stage 1, 2, and 3. The kit may also include instructions for administering the compounds.

Example 10

Methods of Assessing a Risk of Developing Gastric or Non-Gastric OG-Associated Disease A "correlation test" is utilized in which the presence of Og or Og with Hp is compared to the stage of pathology. Diagnostic and quantification tests, either rapid test kits or endoscopic procedures with biopsy, are conducted to determine the presence of Og(+)/Hp(−) infection or Og(+)/Hp(+) infection in a patient. If the bacteria are detected, then imaging techniques well known in the art, such as TEM, can subsequently be employed to determine the stage of infection and pathology: normal mucosal and unremarkable mucosa, mucosal congestion, acute gastritis, chronic gastritis, atrophic gastritis, intestinal metaplasia, dysplasia, or cancer; or MALT versus B cell lymphoma. If the patient is in Stage 2, e.g. atrophic gastritis or intestinal metaplasia, then the patient will probably be unresponsive to eradication therapy so as to completely prevent progression to gastric or non-gastric cancer, and is thus designated "moderate risk". If the patient is in Stage 3, e.g. dysplasia, then the risk is assessed as "high" for the patient to eventually develop gastric and/or non-gastric cancer. And if the patient is unresponsive to Og eradication or Hp eradication treatment, and they maintain a state of continual infection, then their risk may be assessed as "high" for eventually developing gastric and/or non-gastric cancer.

Alternative Method for Lymphoma

Method of assessing risk in a MALT lymphoma occurring and/or progressing and developing into diffuse large B cell lymphoma (DLBCL), or spreading to other mucosal sites (e.g., small intestine, colon, salivary gland, and splenic marginal zone) may comprise testing for a genetic translocation. It is well known in the art that the t(11:18) translocation occurs in approximately 25% of gastric MALT lymphomas and 40% in lung MALT lymphomas. It produces a API2-MALT1 fusion product that appears to protect cells from p53 and FAS induced apoptosis, thus contributing to tumor development.

Translocation of t(11:18) positive cases rarely respond to Hp eradication treatment. Conversely, in t(11:18) translocation negative cases, approximately 75% are responsive. (Du et al, 2006). Tumors with Og infection are expected to have the same response to eradication therapy if they possess this translocation. Therefore, patients displaying Og(+)/Hp(−) or Og(+)/Hp(+) infections should be tested for determining if they possess the t(11:18) translocation. If so, then they can be assessed as "high" for developing MALT or DLBC lymphomas.

Diagnostic Kit

The methods of assessing the risk of Og(+) induced disease may conveniently be performed using a kit. The kit may optionally comprise one or more probes for measuring expression at least one polynucleotide or polypeptide region associated with Og(+) infection, such as 16S rRNA and the arginine aminopeptidase enzyme. A probe may include, for example, a primer pair for performing quantitative PCR, an oligonucleotide that hybridizes to an mRNA or cDNA, corresponding to Og, or an antibody specific for an epitope of an expression product (i.e., mRNA or protein) of a Og. The kit may include instructions for performing a method according to the present invention.

EQUIVALENTS

The invention has been described in greater detail by way of specific patient examples. These examples are offered for illustrative purposes, and are not intended to limit the invention in any manner. Those of skill in the art will readily recognize a variety of non-critical parameters which can be changed or modified to yield essentially the same results using no more than routine experimentation.

REFERENCES

1. Andrew, D. and Aspinall, R., 2001, "IL-7 and not stem cell factor reverses both the increase in apoptosis and the decline in thymopoiesis seen in aged mice," *J Immunol* 166(3): 1524-1530.
2. Attene-Ramos et al, 2006, "Evidence the Hydrogen Sulfide is a Genotoxic Agent," *Mol Cancer Res;* 4(1): 9-13.
3. Du et al, 2006, "Molecular Subtyping of Gastric MALT Lymphomas: Implications for Prognosis and Management," *Gut,* 55: 886-893.
4. Ece et al., 2005, "Does Infection Play a Role in Lung Cancer?", *Respiratory Medicine,* 99(10): 1258-1262.
5. Fox et al., 2007, "Inflammation, Atrophy, and Gastric Cancer," *J of Clin Investigation,* 117(1): 60-69.
6. Huycke, M. and Gaskins, H., "Commensal Bacteria, Redox Stress, and Colorectal Cancer: Mechanisms and Models," *Exp Biol Med,* 229: 586-597.
7. Leedham et al., 2005, "From gene mutations to tumors-stem cells in gastrointestinal carcinogenesis," *Cell Prolif.,* 38: 387-405.
8. Mager, D. L., 2006, "Bacteria and cancer: cause, coincidence or cure? A review," *J Translational Medicine,* 4:14.
9. Prinz et al., 2006, "*H. pylori* and gastric cancer: Shifting the global burden,"*World J of Gastroenterology,* 12(34): 5458-5464.
10. Ruskone-Fourmestraux et al, 2001, "Predictive factors for regression of gastric MALT lymphoma after anti-*Helicobacter pylori* treatment," *Gut,* 48: 297-303
11. Toyokawa et al., 2009, "Eradication of *Helicobacter pylori* infection improved gastric mucosal atrophy and prevented progression of intestinal metaplasia, especially in elderly population: A long-term prospective cohort study," *J Gastroenterol Hepatol.*
12. Walker, M. W., 2003, "Is intestinal metaplasia of the stomach reversible?" *Gut,* 52: 1-4.
13. Yang et al, 2009, "*H. pylori* eradication prevents the progression of gastric intestinal metaplasia in reflux esophagitis patients using long-term esomeprazole," *Am J Gastroenterol,* 104(7): 1642-9.
14. Zhang et al, 2009, "Anti-*Helicobacter pylori* therapy followed by celecoxib on progression of gastric precancerous lesions," *World J Gastroenterol,* 15(22): 2731-8.

I claim:

1. A method of treatment of a human subject suffering from adenocarcinoma or lymphoma associated with an *Okadaella gastrococcus* infection in the absence of an *Helicobacter pylori* infection, said method comprising administering to the subject:
    a first plurality of antibiotics comprising at least ampicillin or amoxicillin and one or more of a tetracycline, a quinolone, and rifampicin, and at least one proton pump inhibitor selected from the group consisting of omeprazole, lansoprazole, rabeprazole, pantoprazole, esomeprazole and zegarid in combination for two weeks,
    and then administering to the subject a second plurality of antibiotics comprising at least ampicillin or amoxicillin and one or more of a tetracycline, a quinolone, and rifampicin, and at least one proton pump inhibitor selected from the group consisting of omeprazole, lansoprazole, rabeprazole, pantoprazole, esomeprazole and zegarid in combination for four weeks,
    wherein the administering is sufficient to reduce and/or eradicate the presence of *Okadaella gastrococcus* in the subject.

2. The method according to claim 1, wherein the tetracycline is doxycycline.

3. The method according to claim 1, wherein the lymphoma comprises a Stage $I_E$, $I_{E1}$ or $I_{E2}$ lymphoma.

4. The method of claim 1, wherein the subject suffers from a Stage 1 adenocarcinoma or lymphoma, and wherein the first plurality of antibiotics comprises amoxicillin and a tetracycline, the second plurality of antibiotics comprises amoxicillin and rifampicin, and wherein the method, following the administering to the subject of the first plurality of antibiotics and at least one proton pump inhibitor in combination for two weeks, and the administering to the subject of the second plurality of antibiotics and at least one proton pump inhibitor in combination for four weeks, comprises:
    administering one or more proton pump inhibitors to the subject for at least four weeks.

5. The method of claim 1, wherein the subject suffers from a Stage 2 adenocarcinoma or lymphoma, and wherein the first plurality of antibiotics comprises amoxicillin and a tetracycline, the second plurality of antibiotics comprises amoxicillin and rifampicin, and wherein the method, following the administering to the subject of the first plurality of antibiotics and at least one proton pump inhibitor in combination for two weeks, and the administering to the subject of the second plurality of antibiotics and at least one proton pump inhibitor in combination for four weeks, comprises:
    administering one or more proton pump inhibitors to the subject for at least four weeks.

6. The method of claim 1, wherein, the subject suffers from a Stage 3 adenocarcinoma or lymphoma, and wherein the first plurality of antibiotics comprises amoxicillin and a tetracycline, the second plurality of antibiotics comprises amoxicillin and rifampicin, and wherein the method, following the administering to the subject of the first plurality of antibiotics and at least one proton pump inhibitor in combination for two weeks, and the administering to the subject of the second plurality of antibiotics and at least one proton pump inhibitor in combination for four weeks, comprises:

administering in combination a tetracycline, rifampicin, and one or more proton pump inhibitors to the subject until the Stage 3 adenocarcinoma or lymphoma is resolved.

7. The method of claim 1, comprising detecting *Okadaella gastrococcus* in a sample from the subject, wherein the detection of said *Okadaella gastrococcus* in the sample is indicative of the presence of the disease or disorder.

8. The method of claim 7, wherein the method comprises detecting *Okadaella gastrococcus* in the sample by microscopic analysis to detect *Okadaella gastrococcus* by morphology or staining, and/or by selective amplification of *Okadaella gastrococcus* DNA or *Okadaella gastrococcus* RNA, and/or antibody detection.

9. The method according to claim 7, wherein the sample comprises a body tissue of the subject being tested.

10. The method according to claim 7, wherein the sample comprises a body fluid of the subject being tested.

11. The method of claim 1, comprising:
detecting the presence of adenocarcinoma or lymphoma associated with an *Okadaella gastrococcus* infection in a subject; and
assessing a stage of the adenocarcinoma or lymphoma.

12. The method of claim 1, comprising administering the first plurality of antibiotics and at least one proton pump inhibitor sequentially and/or the second plurality of antibiotics and at least one proton pump inhibitor sequentially.

13. The method of claim 1, comprising administering the first plurality of antibiotics and at least one proton pump inhibitor simultaneously and/or the second plurality of antibiotics and at least one proton pump inhibitor simultaneously.

* * * * *